United States Patent [19]

Dyllick-Brenzinger et al.

[11] Patent Number: 5,352,843
[45] Date of Patent: Oct. 4, 1994

[54] PREPARATION OF β-NAPHTHYL BENZYL ETHER

[75] Inventors: Rainer Dyllick-Brenzinger, Weinheim; Ulf Baus, Dossenheim, both of Fed. Rep. of Germany

[73] Assignee: BASF Aktiengesellschaft, Ludwigshafen, Fed. Rep. of Germany

[21] Appl. No.: 69,154

[22] Filed: May 28, 1993

[30] Foreign Application Priority Data

Jun. 6, 1992 [DE] Fed. Rep. of Germany ....... 4218767

[51] Int. Cl.$^5$ ............................................. C07C 43/02
[52] U.S. Cl. ................................................... 568/632
[58] Field of Search ................................ 568/632, 631

[56] References Cited

U.S. PATENT DOCUMENTS 5,087,743 2/1992 Janssen .

FOREIGN PATENT DOCUMENTS 1579320 11/1980 United Kingdom .

OTHER PUBLICATIONS

J. Amer. Chem. Soc. 42, (1920) 2059–2072.
J. Amer. Chem. Soc. 85 (1963), 1148–1154.
Chem. Abstr. vol. 71 (1969), 101529a.

Primary Examiner—Alan Siegel
Attorney, Agent, or Firm—John H. Shurtleff

[57] ABSTRACT

A process for preparing β-naphthyl benzyl ether comprises reacting β-naphthol essentially in the absence of water with an alkali metal carbonate or an alkaline earth metal carbonate and benzyl chloride in an inert water-miscible solvent at from 0° to 200° C.

5 Claims, No Drawings

PREPARATION OF β-NAPHTHYL BENZYL ETHER

The present invention relates to a novel process for preparing β-naphthyl benzyl ether by reacting β-naphthol essentially in the absence of water with an alkali metal carbonate or an alkaline earth metal carbonate and benzyl chloride in an inert water-miscible solvent.

J. Amer. Chem. Soc. 42 (1920), 2059–2072, discloses a process for preparing β-naphthyl benzyl ether by reacting the sodium salt of β-naphthol with benzyl chloride in aqueous solution in a 50% yield.

J. Amer. Chem. Soc. 85 (1963), 1148–1154, discloses a process for preparing β-naphthyl benzyl ether by reacting the sodium salt of β-naphthol with the strongly lachrymatory benzyl bromide in dimethylformamide or dimethyl sulfoxide in yields of 97% and 95% respectively.

Chem. Abstr. 71 (1969), 101 529a, discloses the reaction of β-naphthol with benzyl chloride in the presence of oxiranes, glycidyl ethers and catalytic amounts of amines, which leads to the β-naphthyl benzyl ether in a 60% yield.

GB-A-1 579 320 describes a process for preparing β-naphthyl benzyl ether in a yield up to 90% by reacting the sodium salt of β-naphthol with benzyl bromide using phase transfer catalysts.

The prior art processes have the disadvantage of the strongly lachrymatory benzyl bromide as reactant and of using soluble and therefore difficult-to-remove ancillaries. In some cases, moreover, the yields leave something to be desired.

It is an object of the present invention to remedy the aforementioned disadvantages.

We have found that this object is achieved by a novel and improved process for preparing β-naphthyl benzyl ether, which comprises reacting β-naphthol essentially in the absence of water with an alkali metal carbonate or an alkaline earth metal carbonate and benzyl chloride in an inert water-miscible solvent at from 0° to 200° C.

The process of the invention can be carried out as follows:

At from 0° to 200° C., preferably from 60° to 150° C., particularly preferably from 80° to 120° C., and essentially in the absence of water, ie. in the presence of from 0 to 1% by weight, preferably from 0 to 0.1% by weight, particularly preferably from 0 to 0.01% by weight, the β-naphthol is admixed with an alkali metal carbonate or an alkaline earth metal carbonate in an inert water-miscible solvent and then with benzyl chloride, for example by dropwise addition.

The reaction is carried out essentially in the absence, ie. in the presence of from 0 to 1% by weight, preferably from 0 to 0.1% by weight, particularly preferably from 0 to 0.01% by weight, but very particularly preferably in the absence, of oxiranes, glycidyl ethers, amines or phase transfer catalysts at from 0.001 to 50 bar, preferably from 0.1 to 5 bar, particularly preferably at normal (atmospheric) pressure.

The molar ratio of β-naphthol to benzyl chloride is in general from 0.5:1 to 1.5:1, preferably from 0.7:1 to 1.2:1, particularly preferably from 0.8:1 to 1.1:1.

The molar ratio of β-naphthol to carbonate is in general from 0.01:1 to 1:1, preferably from 0.1:1 to 0.9:1, particularly preferably from 0.5:1 to 0.8:1.

Suitable alkali and alkaline earth metal carbonates include lithium carbonate, sodium carbonate, potassium carbonate, rubidium carbonate, cesium carbonate, beryllium carbonate, magnesium carbonate, calcium carbonate, strontium carbonate and barium carbonate, preferably lithium carbonate, sodium carbonate, potassium carbonate, magnesium carbonate and calcium carbonate, particularly preferably sodium carbonate, potassium carbonate, magnesium carbonate and calcium carbonate.

Suitable inert water-miscible solvents include ketones such as acetone and methyl ethyl ketone, preferably acetone, cyclic ethers such as tetrahydrofuran and dioxane, preferably tetrahydrofuran, nitriles such as acetonitrile, sulfoxides such as dimethyl sulfoxide and/or formamides such as dimethylformamide, methylethylformamide, diethylformamide, dimethylacetamide and diethylacetamide, preferably dimethylformamide.

After the reaction has ended, the residue (salt) is filtered off and the hot (about 30°–100° C.) filtrate admixed with water to the onset of cloudiness (ie. to the onset of crystallization). Then the mixture can be allowed to cool down, for example to room temperature at 18°–25° C. or by cooling to 0°–10° C. The precipitated product, the β-naphthyl benzyl ether, can be filtered off and dried. The product thus obtained can be obtained in yields above 90%, frequently in yields above 95%, in a pure form containing from 0 to 3% by weight, preferably from 0 to 1%, particularly preferably from 0 to 0.5% by weight, of impurities.

β-Naphthyl benzyl ether is used for example for manufacturing thermal papers (Mitsubishi paper), for example for fax machines, recorders, etc. The function of this compound is to speed the color reaction without taking part in the reaction (solvent or sensitizer).

EXAMPLES

Example 1

28.2 g (200 mmol) of β-naphthol and 30.4 g (220 mmol) of potassium carbonate were mixed in 80 ml of dimethylformamide, 27.8 g (220 mmol) of benzyl chloride were added dropwise, and the mixture was heated at 120° C. for 2 hours. The residue formed was filtered off, and the filtrate was admixed with water to the onset of cloudiness. Filtration of the cold mixture and drying of the solid gave 44.6 g (95%) of β-naphthyl benzyl ether; melting point: 101° C.

Examples 2 to 6

Example 1 was repeated with other solvents. The quantities of reactants and solvents, the reaction temperature and reactivity and also the yields are shown below in the Table.

TABLE

| Example 2 | Example 3 | Example 4 | Example 5 | Example 6 |
|---|---|---|---|---|
| Diethyl ketone | Isopropanol | N-Methylpyrrolidone | DMF | Dimethylacetamide |
| 150 ml | 150 ml | 150 ml | 150 ml | 150 ml |
| 28.8 g of 2-naphthol | 28.2 g of 2-naphthol | 28.8 g of 2-naphthol | 28.8 g of 2-naphthol | 28.8 g of 2-naphthol |
| (0.2 mol) | (0.2 mol) | (0.2 mol) | 30.4 g of $K_2CO_3$ | 30.4 g of $K_2CO_3$ |
| 27.6 g of $K_2CO_3$ | 16 g of NaOH 50% | 27.6 g of $K_2CO_3$ | (0.22 mol) | 27.8 g of benzyl |
| (0.2 mol) | (0.2 mol) | 3 g of NaI | 27.8 g of benzyl | chloride |

TABLE-continued

| Example 2 | Example 3 | Example 4 | Example 5 | Example 6 |
| --- | --- | --- | --- | --- |
| 3 g of NaI | 25.3 g of benzyl chloride (0.2 mol) | 25.3 g of benzyl chloride | chloride (0.22 mol) | |
| 25.3 g of benzyl chloride (0.2 mol) | | | | |
| 80° C., 8 h | 70° C., 3.5 h | 80° C., 7 h | 120° C., 2 h | 120° C., 2 h |
| 23.3 g = 49% yield | 23.1 g = 49% yield | 34.8 g = 74% yield | 44.6 g = 95% yield | 43.5 = 93% yield |

We claim:

1. A process for preparing β-naphthyl benzyl ether which comprises:

reacting β-naphthol essentially in the absence of water with an alkali metal carbonate or an alkaline earth metal carbonate and benzyl chloride in an inert water-miscible solvent at from 60° C. to 200° C.; and after the reaction has ended, admixing the reaction mixture with water at a temperature of 30° C. to 110° C. only to the onset of crystallization of the β-naphthyl benzyl ether product and thereafter cooling the reaction mixture to a temperature of from 0° C. to 25° C. to cause crystallization and precipitation of said ether product.

2. A process for preparing β-naphthyl benzyl ether as claimed in claim 1, wherein the reaction is carried out at from 60° to 150° C.

3. A process for preparing β-naphthyl benzyl ether as claimed in claim 1, wherein the inert water-miscible solvent used is a ketone, a cyclic ether, a nitrile, a sulfoxide or a formamide.

4. A process as claimed in claim 1, wherein the reaction is carried out at a temperature of from 80° to 120° C. and at atmospheric pressure.

5. A process as claimed in claim 1, wherein the inert solvent is selected from the group consisting of N-methylpyrrolidone, dimethyl formamide and dimethylacetamide.

* * * * *